US00PP09383P

United States Patent [19]

Hanes

[11] Patent Number: Plant 9,383

[45] Date of Patent: Nov. 21, 1995

[54] GERANIUM NAMED 'AMERICANA DEEP ROSE'

[75] Inventor: Mitchell E. Hanes, Morgan Hill, Calif.

[73] Assignee: Goldsmith Seeds, Inc., Gilroy, Calif.

[21] Appl. No.: 364,873

[22] Filed: Dec. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Henderson & Sturm

[57] ABSTRACT

A new geranium cultivar particularly distinguished by green foliage, deep rose flower with a center spot color, and semi-double flowers on large umbels, fast rooting and a bigorous like growth habit.

1 Drawing Sheet

BACKGROUND OF THE NEW PLANT

The present invention comprises a new and distinct cultivar of geranium, botanically known as *Pelargonium hortorum* Bailey,and hereinafter referred to by the cultivar name Americana Deep Rose. The new cultivar is propagated from a seedling resulting form the cross of 3080-2, a breeding line developed by Goldsmith Seeds Inc., used as the seed parent and the variety Fox (U.S. Plant Pat. No. 7,083), which was used as the pollen parent.

Americana Deep Rose is a product of a planned breeding program intended to create new geranium cultivars with deep rose colored flowers that have a reddish macule, semi-double flower from, green foliage, vigorous growth and superior cutting productivity.

The new cultivar was created in 1992 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

Figure 1:
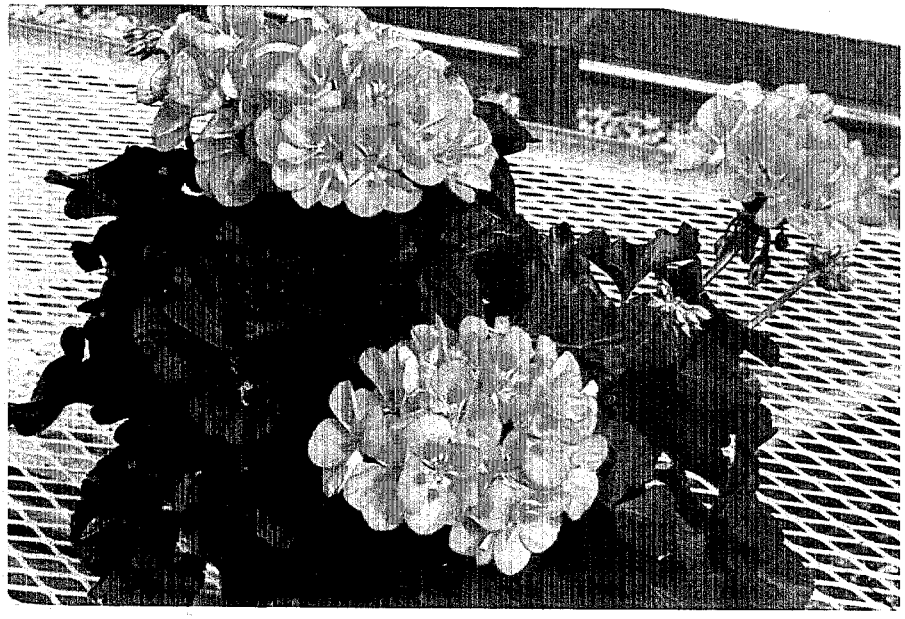
Figure 2:
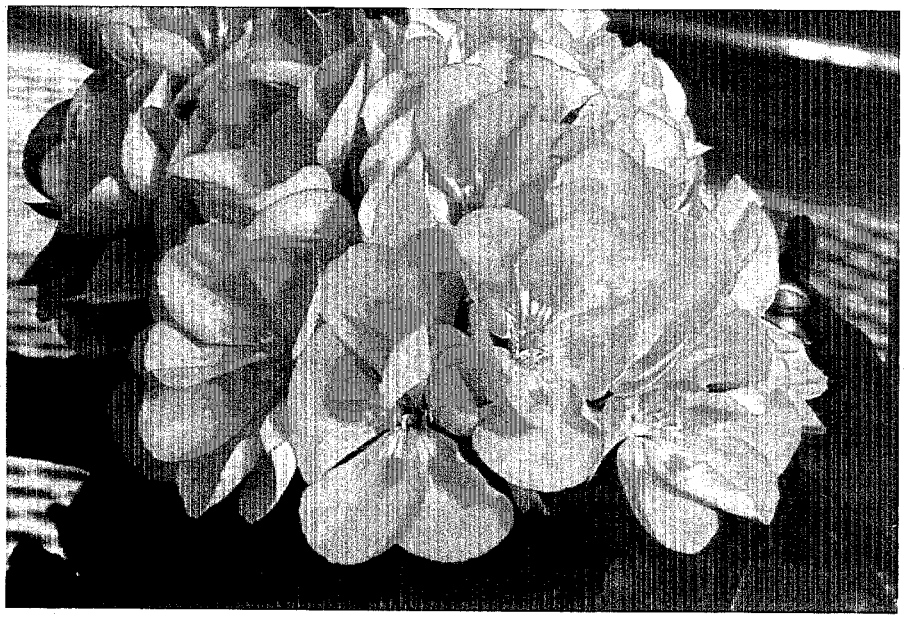

FIG. 1 shown overall plant habit;

FIG. 2 illustrates the mature flower.

DESCRIPTION OF THE NEW CULTIVAR

The following detailed descriptions set forth the distinctive characteristics of Americana Deep Rose. The data which defines these characteristics were collected from asexual reproductions carried out by Goldsmith Seeds, Inc. in Gilroy, Calif. The plant history was taken on 24 week old plants, blossomed under natural light in a structure covered with a screen material that provides shade at 55%. Color readings were taken outside (in Gilroy, Calif.) on Sep. 1, 1994 at 4:00 p.m. under indirect ambient light. Color references are primarily to The R.H.S. Colour Chart of The Royal Horticultural Society of London (R.H.S.).

The Plant

Classification:

*Botanical.*—*Pelargonium hortorum* Bailey.

*Commercial.*—Zonal geranium.

Form: Plant grows in a mound like habit.

Height: 26 to 35 cm., as a 21 inch container plant, excluding blooms.

Strength: Good cutting productivity. Good shipping ability as rooted or unrooted cuttings.

Foliage: Abundant quantity

*Leaves.*—Size: Diameter about 9 cm. Shape: Rounded cordate with occasional upfolding between veins. Margin: Irregularly crenate. Texture: Leathery and pubescent on both surfaces, especially along veins. Ribs and veins: Distinctly palmate, 4.5 to 4.8 cm. long Color: Upper side: Green without zonation Under side; Lighter green color, Ribs and veins not prominently different from upper surface. Petioles: About 8.5 to 10.5 cm in length.

The Bud

Size:

*Diameter.*—About 4.5 mm

*Length.*—About 2.5 cm to 2.8 cm at time of bud opening.

Shape: Pointed ovoid

Sepals: 5 in number, flat behind petals. Pointed linear lanceolate, R.H.S. 144A in an open flower.

The Flower

Blooming habit: Continuous througout the year.

Size: Approximately 5 cm in diameter.

Form: Cup-shaped when bloom first opens, later flattening to shallow cup shape with maturity.

Petals; 5 imbricate outer petals, 2.1–2.5 cm wide and approximately 2.7 cm long. Innter smaller petaloids of varying shape. Both the outer petals and inner petaloids are 67 B-C (R.H.S.) with a darker colored petal spot in the sub-center of the petals, 57A. Veins slightly darker than interveinal regios. Color changing little with age. Underside of petals lighter and the veins are more prominent. Petals and petaloids soft and satiny.

Pedicel: Approximately 3 cm in length.

Persistence: Older flower petals have a tendency to shatter.

Inflorescence

Type: An umbel composed of approximately 34 flowers, erect or laterally ascending.

Peduncle: Approximately 16–22 cm in length, mostly 18 cm, green in color.

Reproductive Organs

Stamens:

*Anthers.*—8–11 positioned below the mature stigma, dull red prior to anthesis.

*Filaments.*—White near base and mid length, graduating to dull red near anther.

*Pollen.*—Orange in color.

Pistil:

*Number.*—1.

*Length.*—Approximately 8 mm.

*Stigma.*—5 linear lobes of near equal length, curling back toward ovary, purplish-red.

*Style.*—Length: About 4 mm Color: Purplish red.

*Ovaries.*—At anthesis, densely pubescent with white hairs, oblong. Green drying to a light brown at maturity.

Fruit.—Partially fertile.

I claim:

1. A new and distinct cultivar of geranium substantially as herein shown and described, named Americana Deep Rose, that is characterized by: green foliage, deep rose flower with a center spot color, and semi-double flowers on large umbels, fast rooting and a bigorous growth habit.

* * * * *